US011872360B2

(12) United States Patent
Wang et al.

(10) Patent No.: US 11,872,360 B2
(45) Date of Patent: Jan. 16, 2024

(54) CATHETER SYSTEMS AND METHODS FOR FLASHBACK VISUALIZATION AT VARIOUS BLOOD PRESSURES

(71) Applicant: Becton, Dickinson and Company, Franklin Lakes, NJ (US)

(72) Inventors: Bin Wang, Sandy, UT (US); Jonathan Karl Burkholz, Salt Lake City, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 539 days.

(21) Appl. No.: 17/075,392

(22) Filed: Oct. 20, 2020

(65) Prior Publication Data

US 2021/0138202 A1 May 13, 2021

Related U.S. Application Data

(60) Provisional application No. 62/933,780, filed on Nov. 11, 2019.

(51) Int. Cl.
*A61M 25/06* (2006.01)
*A61M 39/10* (2006.01)

(52) U.S. Cl.
CPC .... *A61M 25/0693* (2013.01); *A61M 25/0606* (2013.01); *A61M 39/10* (2013.01); *A61M 2039/1077* (2013.01)

(58) Field of Classification Search
CPC .... A61M 2039/062; A61M 2039/0633; A61M 2039/1077; A61M 25/0097;
(Continued)

(56) References Cited

U.S. PATENT DOCUMENTS 6,228,060 B1 * 5/2001 Howell ................. A61M 39/04
604/167.04
10,960,186 B2 * 3/2021 Harding ............ A61M 25/0606
(Continued)

FOREIGN PATENT DOCUMENTS

EP           2364738       9/2011
NO        2017/074679     5/2017
(Continued)

*Primary Examiner* — Quynh-Nhu H. Vu
(74) *Attorney, Agent, or Firm* — Kirton McConkie; Whitney Blair; Kevin Stinger (57) ABSTRACT

A catheter system may include a catheter adapter and a catheter extending distally from the catheter adapter. The catheter system may include a needle assembly, which may include a plug, an outer housing, and an introducer needle. An outer surface of the plug may include multiple grooves, which may be in fluid communication with the introducer needle and configured to receive blood flashback. The grooves may include a first groove having a first surface-area-to-volume ratio, and a second groove having a second surface-area-to-volume ratio. The first surface-area-to-volume ratio may be less than the second surface-area-to-volume ratio. The first groove may have a greater volume than the second groove. The outer housing may seal a top of the first groove and a top of the second groove to prevent blood from flowing out the top of the first groove and the top of the second groove.

7 Claims, 8 Drawing Sheets

(58) Field of Classification Search
CPC .......... A61M 25/0606; A61M 25/0693; A61M 39/06; A61M 39/10
See application file for complete search history.

(56) References Cited

U.S. PATENT DOCUMENTS

| | | | | |
|---|---|---|---|---|
| 2007/0233007 A1* | 10/2007 | Adams | ............... | A61M 25/0097 604/168.01 |
| 2010/0204648 A1* | 8/2010 | Stout | ................. | A61M 39/0208 604/122 |
| 2010/0204660 A1* | 8/2010 | McKinnon | ......... | A61M 25/0043 604/244 |
| 2013/0090607 A1* | 4/2013 | McKinnon | ......... | A61M 39/0693 604/247 |
| 2013/0110055 A1* | 5/2013 | McKinnon | ......... | A61M 39/0606 604/256 |
| 2013/0165868 A1* | 6/2013 | Isaacson | ............ | A61M 25/0693 29/428 |
| 2014/0041496 A1* | 2/2014 | Roehl | ........................ | B26F 1/14 83/30 |

FOREIGN PATENT DOCUMENTS

| | | |
|---|---|---|
| WO | 96/39213 | 12/1996 |
| WO | 2011/097639 | 8/2011 |
| WO | 2012/121843 | 9/2012 |
| WO | 2014/068603 | 5/2014 |
| WO | 2018/080985 | 5/2018 |

* cited by examiner

CATHETER SYSTEMS AND METHODS FOR FLASHBACK VISUALIZATION AT VARIOUS BLOOD PRESSURES

RELATED APPLICATIONS

This application claims the benefit of U.S. Provisional Application No. 62/933,780, filed Nov. 11, 2019, and entitled CATHETER SYSTEMS AND METHODS FOR FLASHBACK VISUALIZATION AT VARIOUS BLOOD PRESSURES, which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. Once placement of the introducer needle within the vasculature has been confirmed, the user may temporarily occlude flow in the vasculature and withdraw the introducer needle, leaving the intravenous catheter in place for future blood withdrawal and/or fluid infusion.

In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter. Accordingly, where the intravenous catheter is at least partially transparent, the user may visualize a small amount of primary blood flashback within the catheter tubing. In some instances, in addition to the primary blood flashback, the user may also visualize a small amount of secondary blood flashback in a chamber proximal to the intravenous catheter, thereby confirming placement of the intravenous catheter within the vasculature.

Presence of a vasculature entrance indicator, such as primary and/or secondary blood flashback, may facilitate successful placement of intravenous catheters. However, visualization of blood flashback by the user can be compromised due to blood pressure variations. Blood pressure may vary significantly different in a static venous versus a tourniquet situation, even in a normal patient. The chamber may not provide noticeable flashback with difficult vein insertions and/or may not provide a lasting signal with high blood pressures.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to catheter devices, systems, and methods for flashback visualization at various blood pressures. In some embodiments, a catheter system may include a catheter assembly, which may include a catheter adapter. In some embodiments, the catheter adapter may include a lumen extending through the catheter adapter. In some embodiments, the catheter assembly may include a catheter extending distally from the catheter adapter.

In some embodiments, the catheter system may include a needle assembly coupled to the catheter assembly. In some embodiments, the needle assembly may include a plug and an outer housing. In some embodiments, the needle assembly may include an introducer needle, which may include a proximal end and a sharp distal tip. In some embodiments, the plug may be monolithically formed as a single unit. In some embodiments, the plug may be press fit within the outer housing.

In some embodiments, the proximal end of the introducer needle may be secured within the plug, and the plug may be a needle hub. In other embodiments, the plug may include a luer adapter, which may be coupled to a proximal end of the outer housing. In some embodiments, the luer adapter may include a luer lock or luer slip connector. In some embodiments, the luer adapter may include a male or female luer connector.

In some embodiments, an outer surface of the plug may include multiple grooves, which may be configured to receive blood flashback. In some embodiments, the grooves may include a first groove and a second groove. In some embodiments, the first groove may have a first surface-area-to-volume ratio, and the second groove may have a second surface-area-to-volume ratio. In some embodiments, the first surface-area-to-volume ratio may be less than the second surface-area-to-volume ratio. In some embodiments, the first groove may have a greater volume than the second groove. In some embodiments, a depth of the first groove may be greater than a depth of the second groove.

In some embodiments, the grooves of the outer surface of the plug may accommodate varying blood pressures and gauges of introducer needles or catheters. In some embodiments, the first groove may be tuned for a different blood pressure or gauge than the second groove. In some embodiments, for tourniquet blood pressure, the first groove, which may have a greater volume than the second groove, may provide a lasting indication of advancement of the introducer needle within the vein. In some embodiments, for venous pressure, the second groove, which may be shallow and have a high surface-area-to-volume ratio compared to the first groove, may provide noticeable blood movement despite low flow rate.

In some embodiments, a proximal end of the first groove may be vented and a proximal end of the second groove may be vented. In some embodiments, the first groove and the second groove may be disposed on a top of the plug, which may facilitate visibility by the user. In some embodiments, the first groove and the second groove may be generally aligned with a longitudinal axis of the plug.

In some embodiments, the outer surface of the plug may include a cavity. In some embodiments, the proximal end of the introducer needle may be disposed within the cavity. In some embodiments, a distal end of the first groove and a distal end of the second groove may be proximate the cavity.

In some embodiments, the grooves may include one or more of the following: the first groove, the second groove, a third groove, a fourth groove, and a fifth groove (which may be referred to in the present disclosure collectively as the "grooves"). In some embodiments, the outer housing may seal a top of the grooves of the following to prevent blood from flowing out the top of the grooves.

In some embodiments, the third groove may have a third surface-area-to-volume ratio. In some embodiments, the first surface-area-to-volume ratio may be less than the third surface-area-to-volume ratio. In some embodiments, the first groove has a greater volume than the third groove.

In some embodiments, the second groove and the third groove may be similar or identical. In some embodiments, the third surface-area-to-volume ratio may be equal to the second surface-area-to-volume and/or a volume of third groove may be equal to the volume of the second groove. In some embodiments, the second groove and the third groove may be disposed on opposing sides of the first groove and/or may be symmetric about the first groove. In some embodiments, a symmetric pattern of the second groove and the third groove about the first groove may facilitate visualization of blood flashback despite gravity bias due to the user's grip technique.

In some embodiments, the fourth groove may have a fourth surface-area-to-volume ratio and/or the fifth groove may have a fifth surface-area-to-volume ratio. In some embodiments, the first surface-area-to-volume ratio may be less than the fourth surface-area-to-volume ratio and/or the fifth surface-area-to-volume ratio. In some embodiments, the first groove has a greater volume than the fourth groove and the fifth groove. In some embodiments, the fourth groove and the fifth groove may be disposed on opposing sides of the first groove and outwardly from the second groove and the third groove. In some embodiments, the fourth groove and the fifth groove may be disposed on opposing sides of the first groove and/or may be symmetric about the first groove. In some embodiments, a symmetric pattern of the fourth groove and the fifth groove may facilitate visualization of blood flashback despite gravity bias due to the user's grip technique.

In some embodiments, the second groove, the third groove, the fourth groove, or the fifth groove may include one or more pockets extending generally perpendicular to a longitudinal axis of the plug and spaced along a length of one or more of the second groove, the third groove, the fourth groove, and the fifth groove.

In some embodiments, one or more of the grooves may be spaced apart by a capillary effect gap, which may pull blood flashback quickly. In some embodiments, the capillary effect gap and/or one or more other portions of the plug may be constructed of a hydrophilic material. In some embodiments, the first groove and the second groove and/or the first groove and the third groove may be spaced apart by the capillary effect gap. In some embodiments, a volume of the capillary effect gap may be less than one or more of the following: the first groove, the second groove, the third groove, the fourth groove, and the fifth groove. In some embodiments, the capillary effect gap may be filled by blood flashback prior to one or more of the following: the first groove, the second groove, the third groove, the fourth groove, and the fifth groove.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
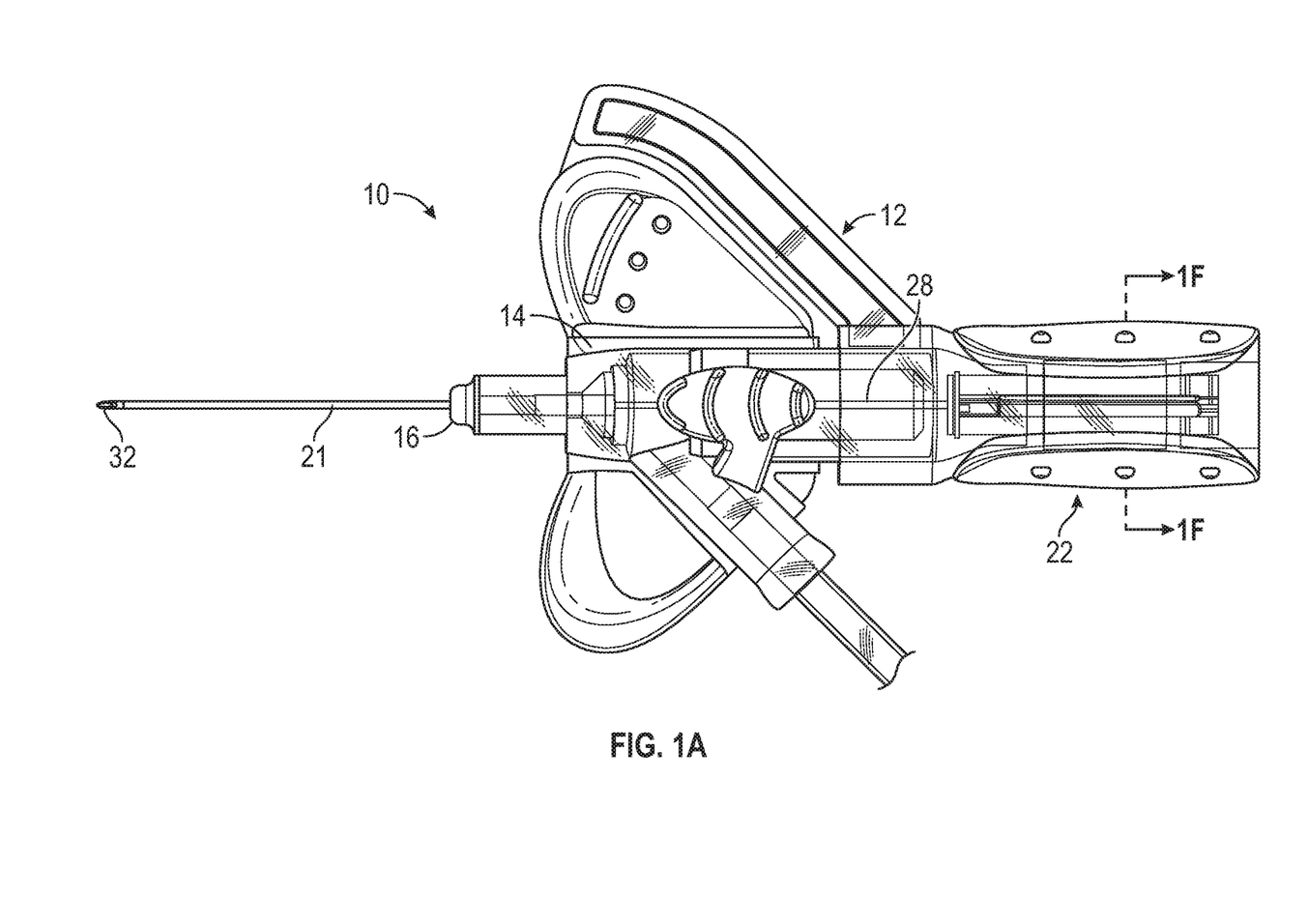
FIG. 1A is an upper perspective view of an example catheter system in an insertion configuration ready for insertion into a patient, according to some embodiments.
Figure 1B:
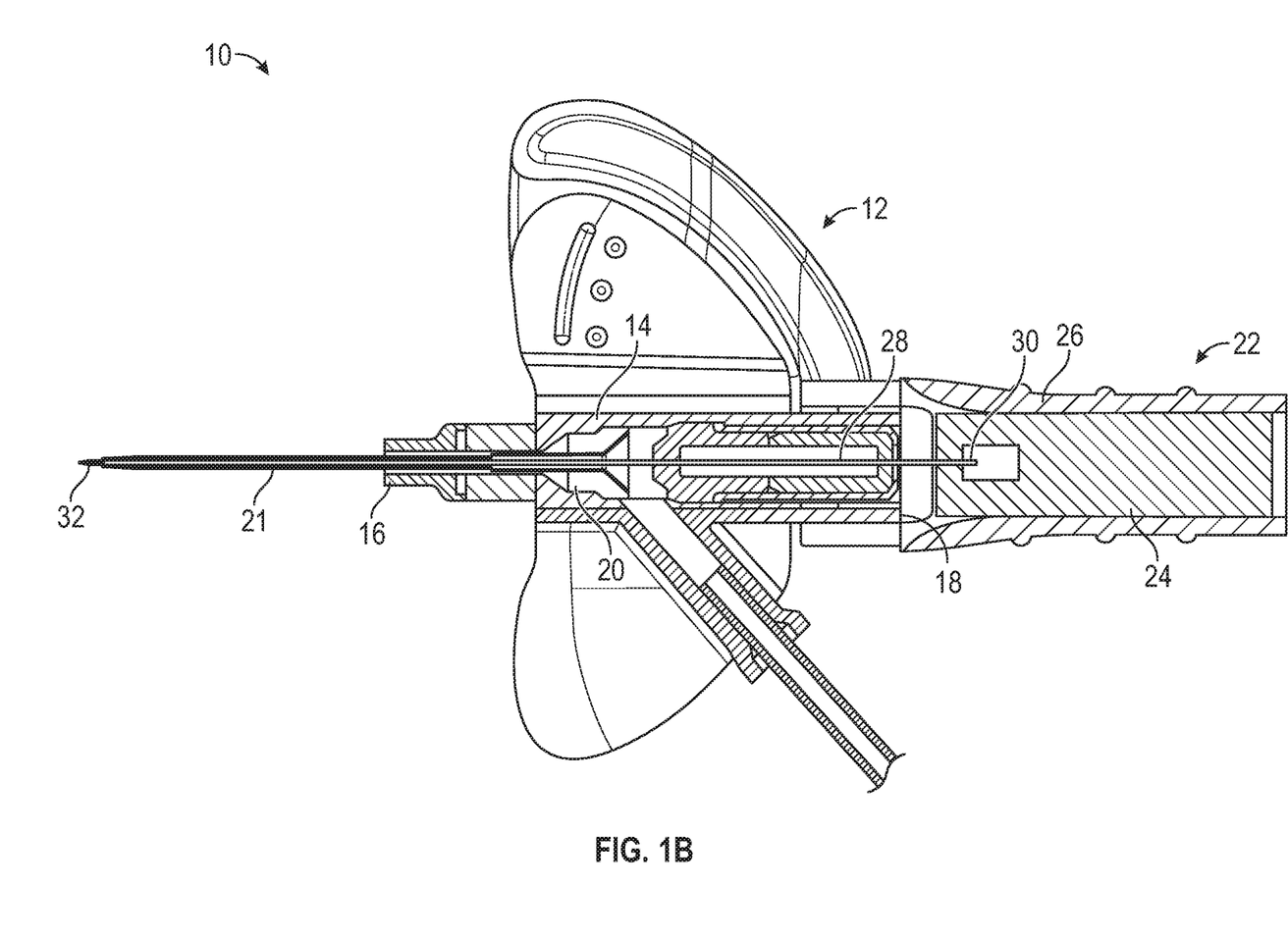
FIG. 1B is a cross-sectional view of the catheter system in the insertion configuration, according to some embodiments.
Figure 1C:
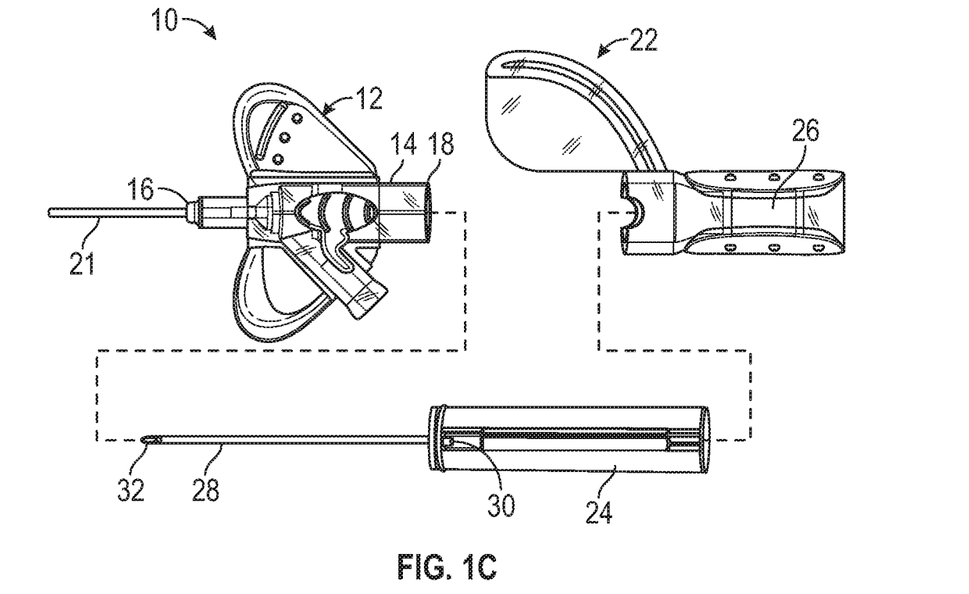
FIG. 1C is an exploded view of the catheter system, according to some embodiments.

Referring now to FIGS. 1A-1C, in some embodiments, a catheter system 10 may include a catheter assembly 12, which may include a catheter adapter 14. In some embodiments, the catheter adapter 14 may include a distal end 16, a proximal end 18, and a lumen 20 extending through the distal end 16 and the proximal end 18. In some embodiments, the catheter system 10 may include a catheter 21, which may extend distally from the distal end 16 of the catheter adapter 14.

In some embodiments, the catheter system 10 may include a peripheral intravenous catheter system, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable peripheral intravenous catheter system. In some embodiments, the catheter system 10 may include an integrated catheter system having an integrated extension tube or a non-integrated catheter system. In some embodiments, the catheter system 10 may include a PICC system or a midline catheter system.

In some embodiments, the catheter system 10 may include a needle assembly 22 coupled to the catheter assembly 12. In some embodiments, the needle assembly 22 may include a plug 24 and an outer housing 26. In some embodiments, the needle assembly 22 may include an introducer needle 28, which may include a proximal end 30 and a sharp distal tip 32. In some embodiments, the plug 24 may be monolithically formed as a single unit. In some embodiments, the plug 24 may be press fit within the outer housing 26. In some embodiments, the proximal end 30 of the introducer needle 28 may be secured within the plug 24, and the plug 24 may be a needle hub.

In other embodiments, the plug 24 may include a luer adapter, which may be coupled to a proximal end of the outer housing, as illustrated, for example, in U.S. Patent Application No. 62/901,631, filed Sep. 17, 2019, entitled "BLOOD COLLECTION DEVICES, SYSTEMS, AND METHODS FACILITATING BLOOD FLASHBACK," which is hereby incorporated by reference in its entirety. In some embodiments, the luer adapter may include a luer lock or luer slip connector. In some embodiments, the luer adapter may include a male or female luer connector.

In some embodiments, an outer surface of the plug 24 may include multiple grooves, which may be configured to receive blood flashback. In some embodiments, in response to the introducer needle 28 being inserted into a vein of a patient, blood flashback may travel from the sharp distal tip 32 through the proximal end 30 of the introducer needle 28 and into the plug 24, where the blood flashback may enter the grooves. Additionally, in some embodiments, the introducer needle 28 may include a notch, which may allow blood flashback to travel between an outer surface of the introducer needle 28 and an inner surface of the catheter 21. In some embodiments, the proximal end 30 of the introducer needle 28 may include a notch or opening.

Figure 1D:
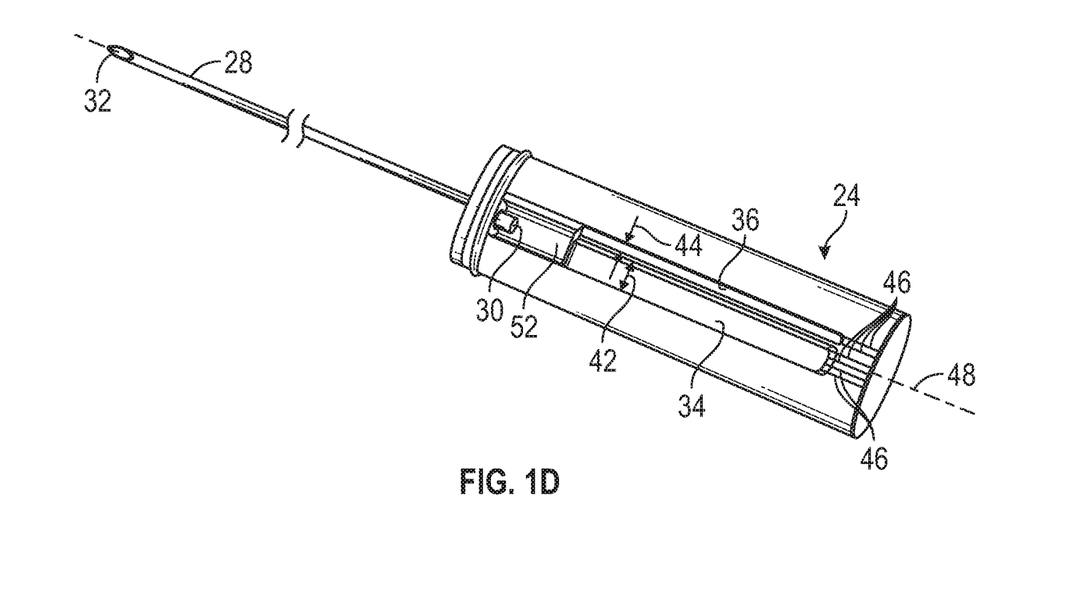
FIG. 1D is an upper perspective view of an example plug, according to some embodiments.
Figure 1E:
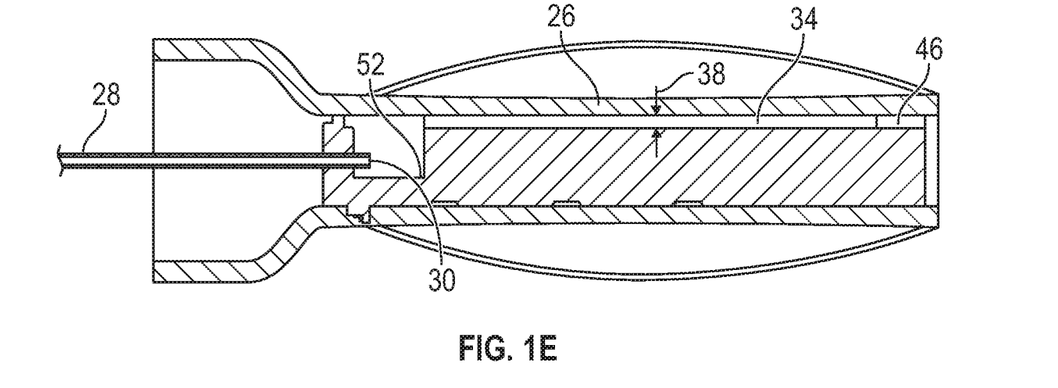
FIG. 1E is another cross-sectional view of an example needle assembly of the catheter system, according to some embodiments.
Figure 1F:
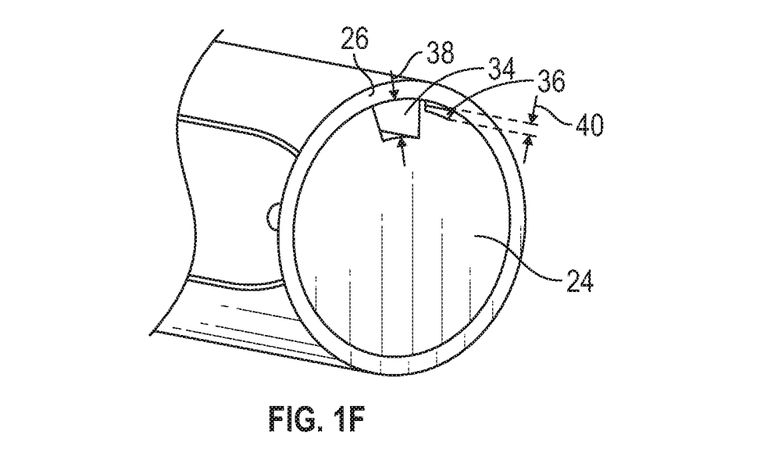
FIG. 1F is cross-sectional view of the catheter system along the line 1F-1F of FIG. 1A, according to some embodiments.

Referring now to FIGS. 1D-1F, in some embodiments, the grooves may include a first groove 34 and a second groove 36. In some embodiments, the first groove 34 may have a first surface-area-to-volume ratio, and the second groove 36 may have a second surface-area-to-volume ratio. In some embodiments, the first surface-area-to-volume ratio may be less than the second surface-area-to-volume ratio. In some embodiments, the first groove 34 may have a greater volume than the second groove 36. In some embodiments, a depth 38 of the first groove 34 may be greater than a depth 40 of the second groove 36. In some embodiments, a width 42 of the first groove 34 may be greater than a width 44 of the second groove 36. In some embodiments, a width 44 of the second groove 36 may be greater than the depth 40 of the second groove 36. In some embodiments, a width 42 of the first groove 34 may be approximately equal to the depth 38 of the first groove 34.

In some embodiments, sides of the first groove 34 may be formed by opposing walls. In some embodiments, the width 42 of the first groove 34 may correspond to a distance between the opposing walls. In some embodiments, sides of the second groove 36 may be formed by other opposing walls. In some embodiments, the walls and the other opposing walls may contact the outer housing 26 to seal flashback blood within the first groove 34 and the second groove 36.

In some embodiments, the width 44 of the second groove 36 may correspond to a distance between the other opposing walls. In some embodiments, one of the opposing walls may correspond to one of the other opposing walls, which may be shared between the first groove 34 and the second groove 36. In some embodiments, the depth 38 of the first groove 34 may correspond to a height of the opposing walls or a distance from a bottom of the first groove 34 to an inner surface of the outer housing 26. In some embodiments, the depth 40 of the second groove 36 may correspond to a height of the other opposing walls or a distance from a bottom of the second groove 36 to the inner surface of the outer housing 26.

In some embodiments, the grooves of the outer surface of the plug 24, such as the first groove 34 and the second groove 36, may accommodate varying blood pressures and gauges of introducer needles or catheters. In some embodiments, the first groove 34 may be tuned for a different blood pressure or gauge than the second groove 36. In some embodiments, for tourniquet blood pressure, the first groove 34, which may have a greater volume than the second groove, may provide a lasting indication of advancement of the introducer needle 28 within the vein. In some embodiments, for venous pressure, the second groove 36, which may be shallow and have a high surface-area-to-volume ratio compared to the first groove 34, may provide noticeable blood movement of the blood flashback despite low flow rate.

In some embodiments, the first groove 34 may facilitate visualization of blood flashback at high blood pressures or large gauges, such as, for example, 18-20 Ga. Low blood pressure may occur in difficult vein access (DVA) situations. In some embodiments, the second groove 36 may facilitate visualization of blood flashback at low blood pressures or small gauges, such as, for example, 24-26 Ga.

In some embodiments, a proximal end of the first groove 34 may be vented and a proximal end of the second groove 36 may be vented. In these embodiments, the plug 24 may include one or more vents 46, which may each include a microgroove that may vent air while preventing blood from passing. In some embodiments, the vents 46 may include a porous membrane that may vent air while preventing blood from passing. In some embodiments, the vents 46 may be proximate the first groove 34 and/or the second groove 36.

Figure 1G:
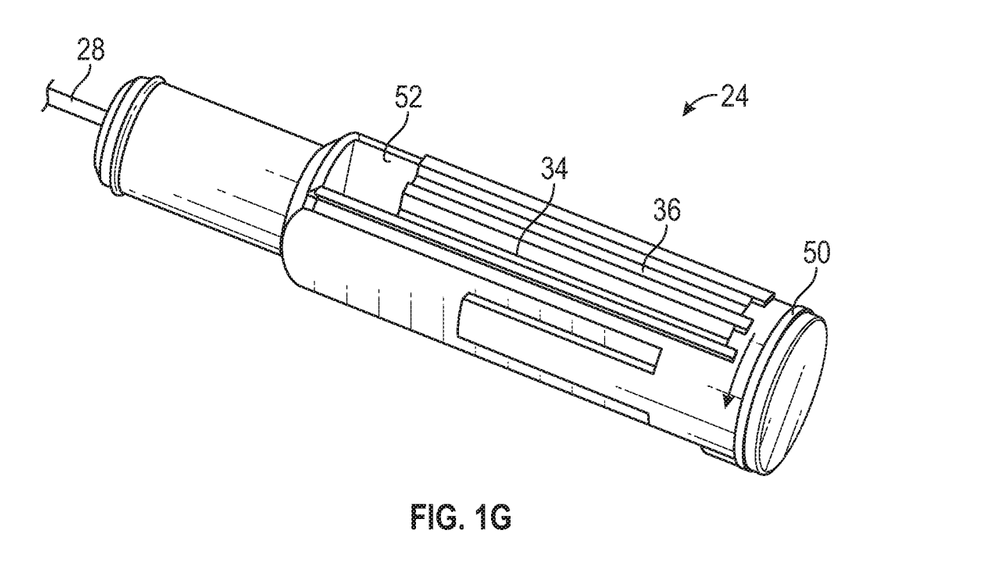
FIG. 1G is an upper perspective view of the plug, according to some embodiments.
Figure 1H:
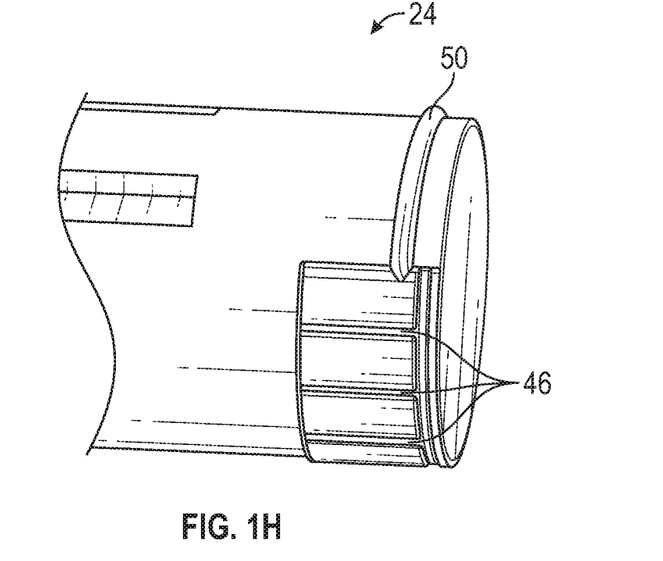
FIG. 1H is a lower perspective view of a portion of the plug, according to some embodiments.
Figure 2A:
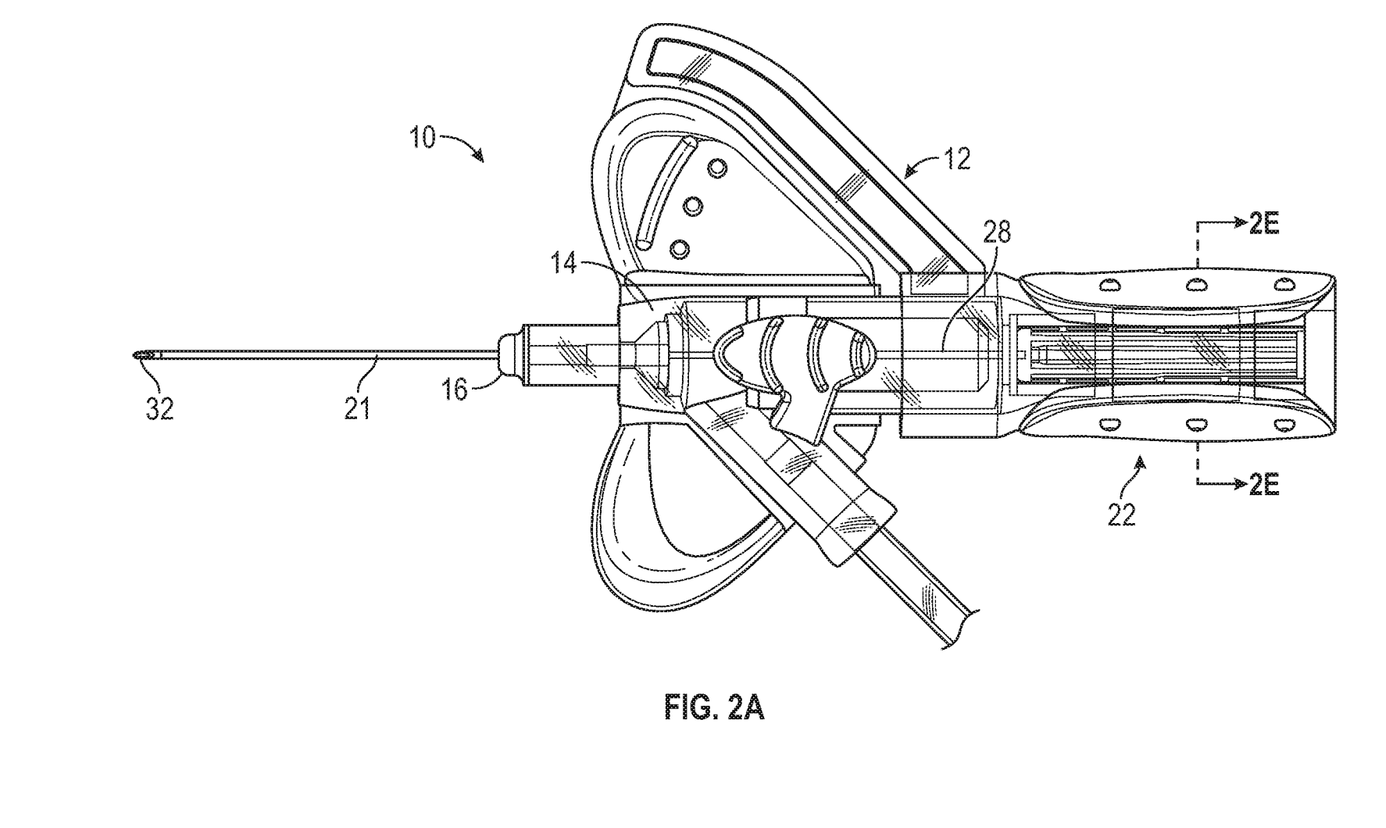
FIG. 2A is an upper perspective view of the catheter system in the insertion configuration ready for insertion into the patient, illustrating another example plug, according to some embodiments.
Figure 2B:
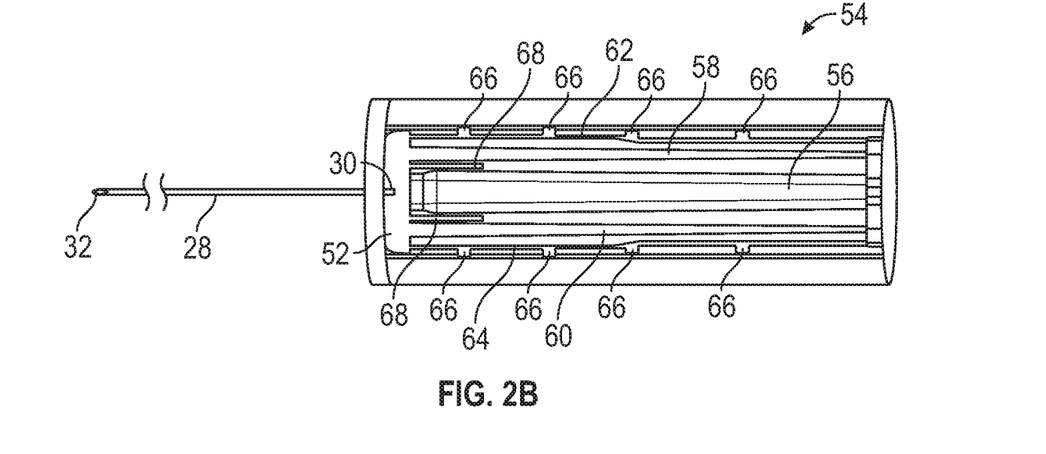
FIG. 2B is a top view of the other plug, according to some embodiments.
Figure 2C:
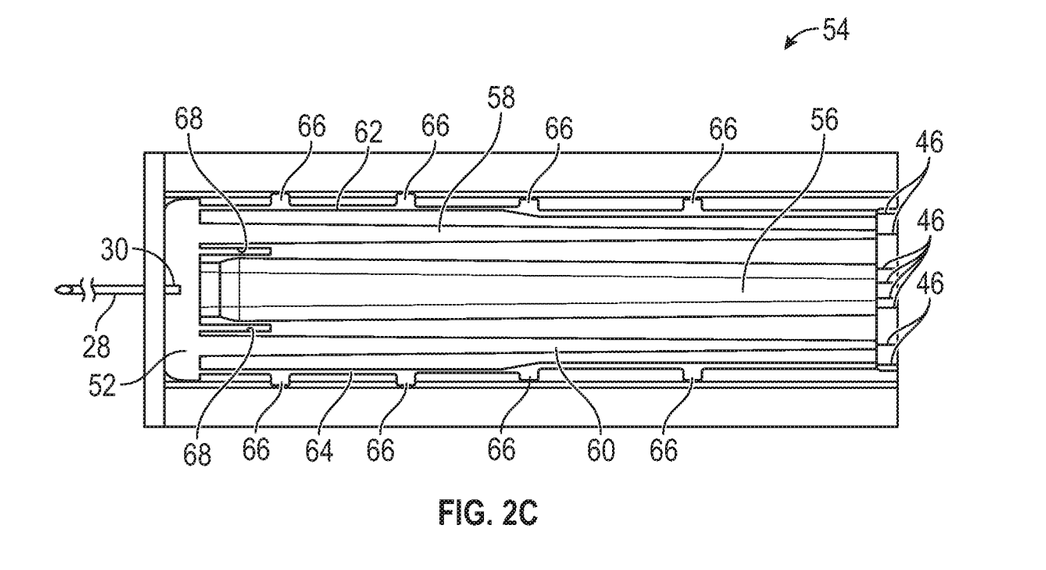
FIG. 2C is an enlarged top view of the other plug, according to some embodiments.
Figure 2D:
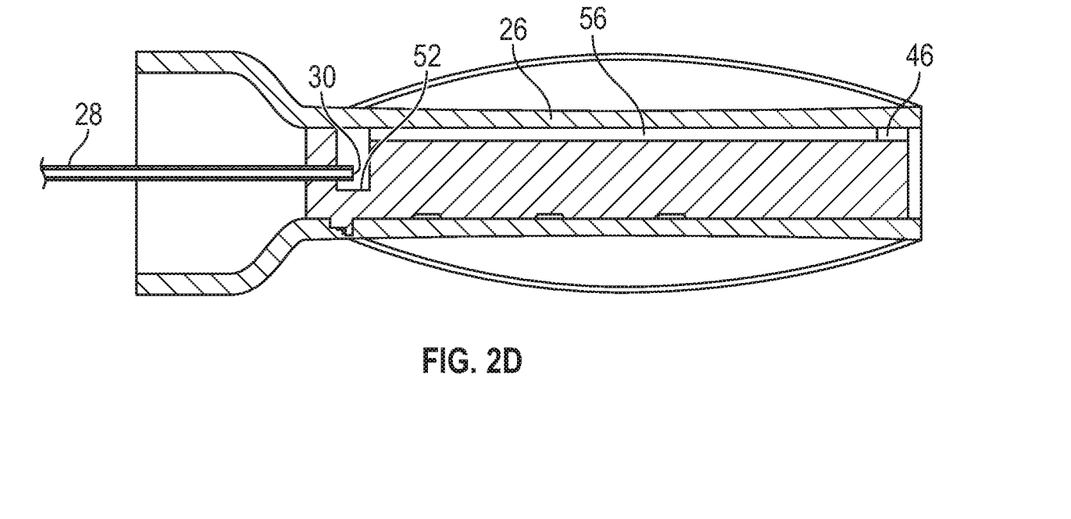
FIG. 2D is a cross-sectional of another example needle assembly of the catheter system, according to some embodiments.
Figure 2E:
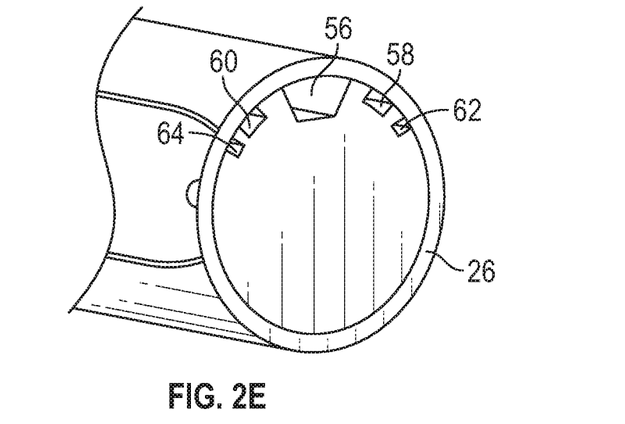
FIG. 2E is a cross-sectional view of the catheter system along the line 2E-2E of FIG. 2A, according to some embodiments.

Referring now to FIGS. 1G-1H, in some embodiments, the vents 46 may be disposed on a bottom of the plug 24, which may facilitate better fluid containment. In some embodiments, flashback may flow proximally through the first groove 34 and the second groove 36 and then down one or more sides of the plug 24 to a location proximate the vents 46. In some embodiments, a proximal end of the plug 24 may include a seal 50, which may include a rib and/or may extend from one side of the vents 46 to the other.

Referring back to FIGS. 1D-1F, in some embodiments, the first groove 34 and the second groove 36 may be disposed on a top of the plug 24, which may facilitate visibility by the user when the catheter system 10 is in the insertion configuration and inserted into the patient. In some embodiments, a bevel of the sharp distal tip 32 may face upwards or towards a top of the catheter system 10, as illustrated in FIG. 1A. In some embodiments, the first groove 34 and the second groove 36 may be generally aligned with a longitudinal axis 48 of the plug 24, which may facilitate easy visualization. In other embodiments, one or more of the grooves may be curved or serpentine to increase blood flashback duration.

In some embodiments, the outer surface of the plug 24 may include a cavity 52. In some embodiments, the proximal end of the introducer needle 28 may be disposed within the cavity 52. In some embodiments, a distal end of the first groove 34 and a distal end of the second groove 36 may be proximate the cavity 52. In some embodiments, the cavity 52 may be deeper than the first groove 34 and/or the second groove 36. In some embodiments, blood travelling through a fluid pathway of the catheter system 10 may be forced from the cavity 52 to an outside of the plug 24, which may improve visibility of the blood within the fluid pathway to the user.

Referring now to FIGS. 2A-2E, a plug 54 of the catheter system 10 is illustrated, according to some embodiments. In some embodiments, the plug 54 may be similar or identical to the plug 24 in terms of one or more included features and/or operation. In some embodiments, an outer surface of the plug 24 may include multiple grooves. In some embodiments, the grooves may include one or more of the following: a first groove 56, a second groove 58, a third groove 60, a fourth groove 62, and a fifth groove 64. In some embodiments, the first groove 56 may be similar or identical to the first groove 34 in terms of one or more included features and/or operation. In some embodiments, the second groove 58 and/or the third groove 60 may be similar or identical to the second groove 36 in terms of one or more included features and/or operation. In some embodiments, the outer housing 26 may seal a top of the grooves of the following to prevent blood from flowing out the top of the grooves.

In some embodiments, a first surface-area-to-volume ratio of the first groove 56 may be less than a second surface-area-to-volume ratio of the second groove 58 and/or a third surface-area-to-volume ratio of a third groove 60. In some embodiments, the first groove 56 has a greater volume than the second groove 58 and/or the third groove 60. In some embodiments, the second groove 58 and the third groove 60 may be similar or identical.

In some embodiments, the second groove 58 and the third groove 60 may be disposed on opposing sides of the first groove 56 and/or may be symmetric about the first groove 56. In further detail, in some embodiments, a shape of the second groove 58 may be a mirror image of a shape of the third groove 60. In some embodiments, a symmetric pattern of the second groove 58 and the third groove 60 about the first groove 56 may facilitate visualization of blood flashback despite gravity bias due to the user's grip technique.

In some embodiments, the first surface-area-to-volume ratio may be less than a fourth surface-area-to-volume ratio of the fourth groove 62 and/or a fifth surface-area-to-volume ratio of the fifth groove 64. In some embodiments, the first groove 34 has a greater volume than the fourth groove 62 and the fifth groove 64. In some embodiments, the fourth groove 62 and the fifth groove 64 may be disposed on opposing sides of the first groove 56 and outwardly from the second groove 58 and the third groove 60. In some embodiments, the fourth groove 62 and the fifth groove 64 may be disposed on opposing sides of the first groove 56 and/or may be symmetric about the first groove 56. In further detail, in some embodiments, a shape of the fourth groove 62 may be a mirror image of a shape of the fifth groove 64. In some embodiments, a symmetric pattern of the fourth groove 62 and the fifth groove 64 may facilitate visualization of blood flashback despite gravity bias due to the user's grip technique.

In some embodiments, the second groove 58, the third groove 60, the fourth groove 62, or the fifth groove 64 may include one or more pockets 66 extending generally perpendicular to a longitudinal axis of the plug 54 and spaced along a length of one or more of the second groove 58, the third groove 60, the fourth groove 62, and the fifth groove 64. In some embodiments, the pockets 66 may facilitate visualization to the user of how far blood flashback has travelled.

In some embodiments, one or more of the grooves may be spaced apart by a capillary effect gap 68, which may pull blood flashback quickly due to the capillary effect. In some embodiments, the capillary effect gap 68 and/or one or more other portions of the plug 54, such as the grooves, may be constructed of a hydrophilic material. In some embodiments, the first groove 56 and the second groove 58 and/or the first groove 56 and the third groove 60 may be spaced apart by the capillary effect gap 68. In some embodiments, a volume of the capillary effect gap 68 may be less than one or more of the following: the first groove 56, the second groove 58, the third groove 60, the fourth groove 62, and the fifth groove 64. In some embodiments, the capillary effect gap 68 may be filled by blood flashback prior to one or more of the following: the first groove 56, the second groove 58, the third groove 60, the fourth groove 62, and the fifth groove 64.

In some embodiments, each of the first groove 56, the second groove 58, the third groove 60, the fourth groove 62, and the fifth groove 64 may be vented and a proximal end of the second groove 36 may be vented. In these embodiments, the plug 54 may include the vents 46. In some embodiments, the plug 54 may be constructed of plastic or another suitable material.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:
1. A catheter system, comprising:
   a catheter assembly, comprising:
      a catheter adapter, comprising a lumen extending through the catheter adapter;
      a catheter extending distally from the catheter adapter; and
   a needle assembly coupled to the catheter assembly, the needle assembly comprising:
      a plug, wherein an outer surface of the plug comprises a first groove having a first surface-area-to-volume ratio and a second groove having a second surface-area-to-volume ratio, wherein the first surface-area-to-volume ratio is less than the second surface-area-to-volume ratio, wherein the first groove has a greater volume than the second groove;
      an outer housing, wherein the outer housing seals a top of the first groove and a top of the second groove to prevent blood from flowing out the top of the first groove and the top of the second groove; and
      an introducer needle, comprising a distal end and a proximal end, wherein the proximal end of the introducer needle is in fluid communication with the first groove and the second groove.

2. The catheter system of claim 1, wherein a depth of the first groove is greater than a depth of the second groove.

3. The catheter system of claim 1, wherein a proximal end of the first groove is vented and a proximal end of the second groove is vented.

4. The catheter system of claim 1, wherein the first groove and the second groove are disposed on a top of the plug.

5. The catheter system of claim 1, wherein the first groove and the second groove are generally aligned with a longitudinal axis of the plug.

6. The catheter system of claim 1, wherein the plug is monolithically formed as a single unit, wherein the plug is press fit within the outer housing, wherein the proximal end of the introducer needle is secured within the plug.

7. The catheter system of claim 1, wherein the outer surface of the plug comprises a cavity, wherein the proximal end of the introducer needle is disposed within the cavity, wherein a distal end of the first groove and a distal end of the second groove are proximate the cavity.

* * * * *